United States Patent [19]

Nakashima et al.

[11] Patent Number: 5,272,243
[45] Date of Patent: Dec. 21, 1993

[54] ORGANOSILICON COMPOUNDS AND METHOD FOR PREPARING SAME

[75] Inventors: Hisataka Nakashima; Tadashi Okawa, both of Chiba, Japan

[73] Assignee: Dow Corning Toray Silicone Co., Ltd., Tokyo, Japan

[21] Appl. No.: 920,234

[22] Filed: Jul. 24, 1992

[30] Foreign Application Priority Data

Jul. 30, 1991 [JP] Japan .................. 3-212643

[51] Int. Cl.$^5$ .................. C08G 77/12; C07F 7/18
[52] U.S. Cl. .................. 528/31; 528/15; 528/32; 556/434; 556/435; 556/451
[58] Field of Search .................. 528/15, 31, 32; 556/434, 435, 451

[56] References Cited

U.S. PATENT DOCUMENTS

| | | | |
|---|---|---|---|
| 3,175,993 | 3/1965 | Weyenberg | 556/434 |
| 4,689,085 | 8/1987 | Plueddemann | 106/287.14 |
| 4,772,675 | 9/1988 | Klosowski et al. | 528/15 |
| 4,849,491 | 7/1989 | Ogawa et al. | 528/15 |
| 5,175,328 | 12/1992 | Okawa et al. | 556/451 |
| 5,194,649 | 3/1993 | Okawa | 556/451 |

FOREIGN PATENT DOCUMENTS 124805 of 0000 European Pat. Off. .
2036499 of 0000 Fed. Rep. of Germany .

*Primary Examiner*—Melvyn I. Marquis
*Assistant Examiner*—Margaret W. Glass
*Attorney, Agent, or Firm*—Robert Spector

[57] ABSTRACT

The linear organosilicon compounds of this invention contain at least two silicon-bonded hydrogen atoms at one of the two terminal positions of the molecule and at least two silicon-bonded hydrolyzable groups at the other terminal position. The compounds are useful as intermediates for preparing organosilicon compounds containing at least two organofunctional groups in each molecule.

4 Claims, No Drawings

ORGANOSILICON COMPOUNDS AND METHOD FOR PREPARING SAME

BACKGROUND OF THE INVENTION

1. Field of the Invention

The present invention relates to novel organosilicon compounds and to a method for preparing these compounds. More specifically, the present invention relates to linear organosilicon compounds containing at least two silicon-bonded hydrogen atoms at one of the molecular terminals and at least two silicon-bonded hydrolyzable groups at the other molecular terminal. The present invention also relates to a method for preparing these compounds.

2. Background Information

Organosilicon compounds containing both silicon-bonded hydrogen and silicon-bonded hydrolyzable groups are already known in the form of trialkoxysilanes. Derivatives of these trialkoxysilanes, including 3-aminopropyltriethoxysilane, 3-glycidoxypropyltrimethoxysilane and vinyltrimethoxysilane among others, are referred to as silane coupling agents. A layer of a silane coupling agent is placed as a primer between an organic resin and an inorganic material to increase the compatibility and bonding between these substrates. Silane coupling agents are also widely used s physical property modifiers for composite materials and as modifiers for organic resins.

U.S. patent application Ser. No. 07/825,706, filed in the names of the present inventors, discloses novel linear organosilicon compounds containing at least two alkoxy groups at one terminal position and a hydrogen atom or an unsaturated hydrocarbon radical at the second terminal position. Both this organosilicon compound and conventional silane coupling agents contain at lest two hydrolyzable groups in each molecule, but only a single organofunctional group. As a result, their properties are not sufficiently manifested in some applications. For example, when an amino-containing trialkoxysilane is used as a modifier for a polyimide resin, due to the presence of only one organofunctional group, hydrolyzable groups can be introduced only at the terminals positions of the polyimide resin molecules, with the result that insufficient modification of the resin is achieved.

SUMMARY OF THE INVENTION

One objective of the present invention is to provide novel linear organosilicon compounds containing at least two silicon-bonded hydrogen atoms at one of the two terminal positions of the molecule and at least two silicon-bonded hydrolyzable groups at the other terminal position. The compounds are useful intermediates for preparing organosilicon compounds containing at least two organofunctional groups in each molecule.

An additional objective of this invention is to provide a method for preparing the present organosilicon compounds,

DETAILED DESCRIPTION OF THE INVENTION

The objectives of this invention are achieved by providing a class of organosilicon compounds exhibiting the general formula

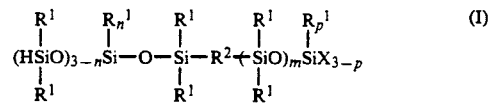

wherein each $R^1$ is individually selected from the group consisting of monovalent hydrocarbon radicals free of aliphatic unsaturation, n is 0 or 1, $R^2$ is a divalent hydrocarbon radical, X is a hydrolyzable group, m is 0 or an integer with a value from 1 to 100, and p is 0 or 1.

The compounds of this invention are prepared by reacting an organosilicon compound II of the general formula

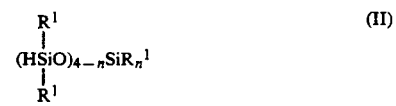

with an organosilicon compound III of the general formula

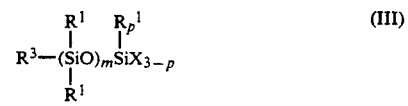

where $R^2$ represents an ethylenically unsaturated monovalent hydrocarbon radical and the molar ratio of organosilicon compound II to organosilicon compound III is at least 1.

The organosilicon compounds of this invention, referred to hereinafter as organosilicon compound I, can be represented by general formula I

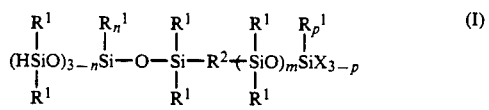

wherein $R^1$, n, $R^2$, X, m, and p are defined in the preceding sections of this specification.

The hydrocarbon radial represented by $R^1$ in formula I are identical or different monovalent hydrocarbon radicals that are free of aliphatic unsaturation. Examples of suitable hydrocarbon radicals include but are not limited to alkyl radicals such as methyl, ethyl, and propyl; aryl radicals such as phenyl, tolyl, and xylyl; and substituted alkyl radicals such as chloromethyl, 3,3,3-trifluoropropyl and perfluoroalkyl. The $R^1$ radicals are preferably individually selected from the group consisting of methyl, phenyl and 3,3,3-trifluoropropyl.

The subscript n has a value of 0 or 1. Organosilicon compound I contains 3 silicon-bonded hydrogen atoms when n is zero and contains 2 silicon-bonded hydrogen atoms when n is one.

The numerical value of this subscript n is the characteristic or distinguishing feature of the present compounds. Because n is zero or one, the organosilicon compounds of this invention contain 2 or 3 silicon-bonded hydrogen atoms at one of the terminal positions of each molecule, making it possible to introduce a total of two or three organofunctional groups at these positions.

$R^2$ represents a divalent hydrocarbon radical, and is exemplified but not limited to alkylene groups such as methylene, ethylene, isopropylene, and chloropropylene. The group represented by X is a hydrolyzable group, and is exemplified by but not limited to alkoxy groups such as methoxy and ethoxy in addition to acetoxy, oxime and amide groups.

The subscript m represents 0 or an integer with a value from 1 through 100. When m is zero, $R^2$ is directly bonded to the silicon atom bearing the hydrolyzable groups. Each increment in the value of m by one adds one additional diorganosiloxane ($R^1{}_2SiO$) unit between $R^2$ and the silicon atom bearing the hydrolyzable groups.

The present organosilicon compounds contain 3 hydrolyzable groups when the value of p is 0 or 2 hydrolyzable groups when p is 1.

Preparation of the Present Organosilicon Compounds

The present compounds are prepared by reacting an organohydrogensiloxane, referred to hereinafter as organosilicon compound II, corresponding to formula II

with organosilicon compound III of the formula

$R^1$, $R^3$, m, n and p are defined in a preceding section of this specification.

When n is 0, organosilicon compound II is a neopentasiloxane containing four silicon-bonded hydrogen atoms per molecule. When n is 1 organosilicon compound II is a tris(diorganohydrogensiloxy)silane containing three silicon-bonded hydrogen atoms per molecule.

Organosilicon compound II can be prepared by known methods.

$R^3$ of organosilicon compound III represents an ethylenically unsaturated monovalent hydrocarbon radial. This radical is preferably alkenyl, contains from 2 to 4 carbon atoms and is exemplified by but not limited to vinyl, allyl, and 2-chloro-2-propenyl. $R^3$ is directly bonded to the silicon atom bearing the hydrolyzable groups when m is zero. On the other hand, each increment in the value of m by one places an additional $R^1{}_2SiO$ unit between $R^3$ and the silicon atom bearing the hydrolyzable groups. $R^3$ preferably contains from 2 to 4 carbon atoms and the value represented by m is preferably from 0 to 4, inclusive.

It should be evident that organosilicon compound III, represented by formula III, contains 3 hydrolyzable groups when p is zero and contains 2 hydrolyzable groups when p is 1.

Vinyltrialkoxysilanes, the compounds represented by formula III when the values of m and p are 0, can be prepared by known methods. When the value of m is at least two, organosilicon compound III can be prepared by a condensation reaction between a tetraalkoxysilane and a diorganopolysiloxane containing alkenyl radicals and silanol groups, such as the type of compounds described in U.S. Pat. No. 4,876,373, the entire contents of which are incorporated herein by reference thereto.

Catalysts typically employed for hydrosilation reactions can be used as catalysts for the reaction between organosilicon compounds II and III. Specific examples of suitable hydrosilation catalysts are metals from the platinum group of the periodic table and compounds of these metals, including but not limited to platinum catalysts such as chloroplatinic acid, alcohol solutions of chloroplatinic acid, platinum/olefin complexes, platinum/vinylsiloxane complexes, and rhodium catalysts such as Wilkinson's complex and rhodium/carbonyl complexes. The catalyst concentration is typically from 1 to 100 weight parts, preferably for 1 to 50 weight parts, based on the metal portion of the catalyst, per 1 million weight parts of combined organosilicon compounds II and III.

The hydrosilation reaction may not occur when the catalyst concentration is less than 1 weight part per million. The rate of the reaction is not accelerated in direct proportion to the catalyst concentration at concentrations greater than about 100 weight parts per million which renders the use of large quantities of this expensive catalyst uneconomical.

The temperature of the hydrosilation reaction is not strictly specified, but usually falls within the range of 25° to 250° C. and preferably within the range of 50° to 150° C. Productivity is impaired at reaction temperatures below 25° C. due to a slow reaction rate. On the other hand, reaction temperatures in excess of 250° C. risk the occurrence of secondary reactions promoted by the hydrosilation reaction catalyst.

Organic solvents for organosilicon compounds II and III can be used as liquid reaction media if desired so long as the objectives of this invention are not adversely affected. Suitable organic solvents include but are not limited to aromatic hydrocarbons such as benzene, toluene, and xylene; aliphatic hydrocarbons such as benzene, toluene, and xylene; aliphatic hydrocarbons such as hexane and heptane; ethers such as tetrahydrofuran and diethyl ether; ketones such as acetone and methyl ethyl ketone; and ester such as ethyl acetate and butyl acetate.

It is crucial that the molar ratio of organosilicon compound II relative to organosilicon compound III in the reaction mixture be at least 1:1 and preferably at least 3:1. A molar ratio of less than 1:1 results in the production of compounds in which several molecules of organosilicon compound III have reacted with the silicon-bonded hydrogen atoms in organosilicon compound II, thereby reducing the yield of the desired organosilicon compound I.

After completion of the addition reaction, organosilicon compound I can be recovered by distillation from the reaction mixture or by distilling out lower boiling liquids under reduced pressure, leaving the desired product in the reactor.

The organosilicon compounds of this invention are useful as an intermediates for the synthesis of organosilicon compounds containing 2 or 3 organofunctional groups and 2 or 3 silicon-bonded hydrolyzable groups in each molecule. This latter type of organosilicon compound can be used as modifiers for various types of organic resins and to improve the adhesion between various types of organic resins and inorganic materials.

EXAMPLES

The following examples describe preferred embodiments of the present compounds and the method for preparing these compounds, and should not be interpreted as limiting the invention defined in the accompanying claims. Unless otherwise specified all parts and percentages are by weight and viscosities were measured at 25° C.

EXAMPLE 1

A four-neck flask equipped with stirrer, reflux condenser, addition funnel, and thermometer was charged with 425.4 g (1.58 mol) of methyltris(dimethylsiloxy)silane and 33.9 mg of a platinum/vinylsiloxane complex, equivalent to a platinum concentration of 4.6 wt %. The platinum/vinylsiloxane complex had been prepared from chloroplatinic acid and 1,3-divinyl-1,1,3,3-tetramethyldisiloxane. The mixture was heated to 80° C. with stirring, at which time 78.1 g (0.527 mol) vinyltrimethoxysilane was added dropwise to the reaction mixture. After the completion of this addition, the reaction was continued for 1.5 hours while the temperature was increased from 80° to 145° C. Distillation of the reaction mixture yielded 178.0 g, equivalent to an 81% yield, of an organosilicon compound of this invention, Ia, with the following formula boiling at 120° C./4 mm Hg.

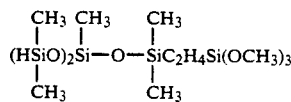

EXAMPLE 2

A four-neck flask equipped with stirrer, reflux condenser, addition funnel, and thermometer was charged with 81.4 g (0.303 mol) methyltris(dimethylsiloxy)silane and 15.5 mg of a platinum/vinylsiloxane complex equivalent to a platinum concentration of 4.6 wt %. The platinum/vinylsiloxane complex had been prepared from chloroplatinic acid and 1,3-divinyl-1,1,3,3-tetramethyldisiloxane. The mixture was heated to 90° C. with stirring, at which time 45.0 g (0.101 mol) of an organosilicon compound with the following formula was added dropwise.

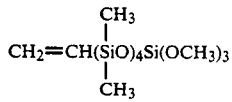

After the completion of this addition, the reaction was continued for 30 minutes while the temperature was increased from 90° to 124° C. The low boiling liquids were then distilled from the reaction mixture under reduced pressure for 3 hours at 140° C./4 mm Hg to yield 68.6 g, equivalent to a 95% yield, of an organosilicon compound of this invention, Ib, with the following formula.

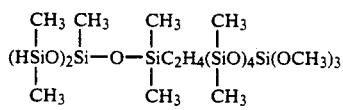

EXAMPLE 3

A four-neck flask equipped with stirrer, reflux condenser, addition funnel, and thermometer was charged with 72.5 g (0.257 mol) ethyltris(dimethylsiloxy)silane and 4.5 mg Wilkinson's complex (RhCl(PPh3)3). The resultant mixture was heated to 95° C. with stirring at which time 13.9 g (0.0857 mol) of allyltrimethoxysilane was added dropwise. Following completion of this addition, stirring of the reaction mixture was continued for 1.2 hours while the temperature was increased from 95° to 140° C. Distillation of low boiling liquids from the reaction mixture for 3 hours at 100° C./25 mm Hg yielded 33.2 g, equivalent to an 87% yield, of organosilicon compound Ic corresponding to the formula

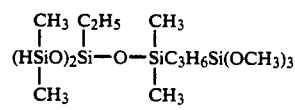

EXAMPLE 4

A four-neck flask equipped with stirrer, reflux condenser, addition funnel, and thermometer was charged with 102.3 g (0.362 mol) of ethyltris(dimethylsiloxy)silane and 16.4 mg of Wilkinson's complex (RhCl(PPh3)3). The mixture was heated to 98° C. with stirring, at which time 55.5 g (0.121 mol) of an organosilicon compound corresponding to the following formula was added dropwise.

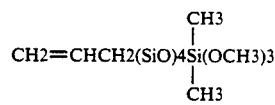

Following completion of this addition, stirring of the reaction mixture was continued for 1.5 hours while the temperature was increased from 98° to 152° C. The low boiling liquids were then distilled from the reaction mixture for 3 hours at 145° C./3 mm Hg to yield 79.9 g, equivalent to an 89% yield, of an organosilicon compound Id corresponding to the formula.

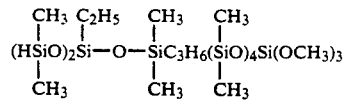

EXAMPLE OF END USE APPLICATION OF ORGANOSILICON COMPOUND IA

The mixture of 108.7 g (0.261 mol) of the organosilicon compound Ia, prepared in Example 1, and 47.3 mg platinum/vinylsiloxane complex, equivalent to a platinum concentration of 4.6 weight percent, was heated to 90° C. in a four-neck flask equipped with stirrer, reflux condenser, addition funnel, and thermometer. The platinum/vinylsiloxane complex had been prepared from chloroplatinic acid and 1,3-divinyl-1,1,3,3-tetramethyldisiloxane. Into this mixture was dripped 80.9 g (0.626 mol) N-trimethylsilylallylamine over a period of 1.2 hours. Following completion of this addition, stirring was continued for 3.5 hours while the temperature was increased from 90° to 170° C. for 3.5 hours. Low boiling liquids were then distilled under reduced pressure from the reaction mixture for 3 hours at 190° C./3 mm Hg to yield 155.8 g, equivalent to an 89% yield, of organosilicon compound (A) corresponding to the formula.

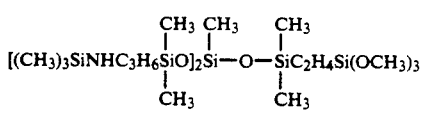 (A)

A solution prepared by dissolving 8.9 g (41.0 mmol) of pyromellitic dianhydride and 0.93 g (6.30 mmol) of phthalic anhydride in 167.6 g of N-methyl-2-pyrrolidinone (NMP) was placed in a four-neck flask equipped with stirrer, reflux condenser, addition funnel, and thermometer. A solution of 29.7 g (44.0 mmol) organosilicon compound (A) in 15 g NMP was added dropwise over 30 minutes following completion of this room temperature for 30 minutes following completion of this addition.

The resulting solution of the polyamic acid was coated on a glass plate. Heating of the coated plate in an oven at 200° C. for 3 hours produced a brown polyimide resin. This polyimide resin adhered strongly to the glass plate.

That which is claimed is:

1. An organosilicon compound exhibiting the general formula

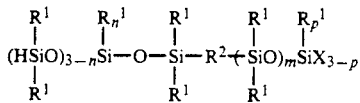 (I)

wherein each $R^1$ is individually selected from the group consisting of monovalent hydrocarbon radical as free of aliphatic unsaturation, n is 0 or 1, $R^2$ is a divalent hydrocarbon radical, X is a hydrolyzabale group, m is 0 or an integer with a value from 1 to 100, and p is 0 or 1.

2. A compound according to claim 1 where each $R^1$ is selected from the group consisting of methyl, phenyl and 3,3,3-trifluoropropyl, $R^2$ is alkylene containing from 2 to 4 carbon atoms and m is 0 or an integer from 1 to 4.

3. A method for preparing an organosilicon compound I of the general formula

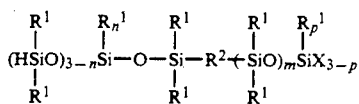 (I)

wherein each $R^1$ is individually selected from the group consisting of monovalent hydrocarbon radicals free of aliphatic unsaturation, n is 0 or 1, $R^2$ is a divalent hydrocarbon radical, X is a hydrolyzable group, m is 0 or an integer with a value from 1 to 100, and p is 0 or 1, said method comprising (1) reacting an organosilicon compound II of the general formula

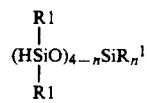 (II)

with an organosilicon compound III of the general formula

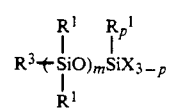 (III)

where $R^3$ represents an ethylenically unsaturated monovalent hydrocarbon radical in the presence of a hydrosilation catalyst, where the molar ratio of organosilicon compound II to organosilicon compound III is at least 1, and (2) isolating organosilicon compound I from the reaction mixture.

4. A method according to claim 3 where each $R^1$ is selected from the group consisting of methyl, phenyl and 3,3,3-trifluoropropyl, $R^3$ is alkenyl containing from 2 to 4 carbon atoms, m is 0 or an integer from 1 to 4 and said hydrosilation catalyst is platinum group metal or a compound of said metal, and organosilicon compounds II and III are reacted at a temperature of from 25° to 250° C.

* * * * *